United States Patent
Eberle

(10) Patent No.: US 8,075,551 B2
(45) Date of Patent: Dec. 13, 2011

(54) SURGICAL COUPLING DEVICE

(75) Inventor: Frank Eberle, Wumberg (DE)

(73) Assignee: EFS—Eberle-Feinwerktechnische Systeme GmbH & Co. KG, Wumberg (DE)

( * ) Notice: Subject to any disclaimer, the term of this patent is extended or adjusted under 35 U.S.C. 154(b) by 0 days.

(21) Appl. No.: 13/095,217

(22) Filed: Apr. 27, 2011

(65) Prior Publication Data
US 2011/0202043 A1    Aug. 18, 2011

Related U.S. Application Data

(63) Continuation of application No. 11/603,550, filed on Nov. 22, 2006.

(30) Foreign Application Priority Data

Nov. 24, 2005  (EP) .................................. 05025706

(51) Int. Cl.
*A61M 39/00* (2006.01)
*F16L 3/13* (2006.01)
*F16L 37/084* (2006.01)

(52) U.S. Cl. ............................... 606/1; 285/921; 285/88

(58) Field of Classification Search ............... 285/81–88, 285/322–324, 921; 606/1
See application file for complete search history.

(56) References Cited

U.S. PATENT DOCUMENTS

| | | | |
|---|---|---|---|
| 3,713,076 A * | 1/1973 | Gabrielian et al. | 439/352 |
| 5,482,331 A * | 1/1996 | Shore | 285/314 |
| 6,431,607 B1 * | 8/2002 | Kittelmann et al. | 285/7 |
| 7,469,933 B2 * | 12/2008 | Swift et al. | 285/86 |
| 7,533,907 B2 * | 5/2009 | Swift et al. | 285/321 |
| 2007/0179477 A1 * | 8/2007 | Danger | 606/1 |

* cited by examiner

*Primary Examiner* — Henry M Johnson, III
*Assistant Examiner* — Andrew Sandefer

(57) ABSTRACT

The present invention relates to a surgical coupling device for detachably connecting a handpiece end to a portion of a surgical instrument, the handpiece end being provided with a recess into which a coupling portion of the instrument can be detachably slid, an interior wall of the recess having formed thereon a locking recess with which a snap type element can be brought into detachable engagement that is supported on the instrument, characterized in that the snap type element is formed on a double-sided rocker which extends substantially in axial direction and has one end on which the snap type element is arranged and has its other end in engagement with a pivot element.

4 Claims, 1 Drawing Sheet

SURGICAL COUPLING DEVICE

CROSS REFERENCE TO RELATED APPLICATIONS

This application is a continuation of U.S. patent application Ser. No. 11/603,550, filed on Nov. 22, 2006, entitled Surgical Coupling Device, and claims priority from European Patent Application 05025706.2, filed on Nov. 24, 2005, both disclosures of which are incorporated herein by reference in their entirety for all purposes.

TECHNICAL FIELD

The invention relates to a surgical coupling device for detachably connecting a handpiece to a surgical instrument.

BACKGROUND INFORMATION

Surgical instruments that are inserted into a handpiece are known in the most different variants. The handpieces are normally connected to a drive, whereby tools or portions of the surgical instruments are drivable, e.g. rotatable. Such surgical instruments may for instance be dental drills or cutters; they may also be designed as shaver instruments for arthroscopy.

It is known from the prior art (see e.g. EP 1 006 898 B1) that the handpiece is provided with a central bore or recess into which a coupling portion or attachment portion of the surgical instrument is inserted. In this process corresponding drive couplings of the handpiece get into engagement with coupling members of the surgical instrument, so that a rotary drive is realized. The surgical instrument is inserted into and locked in the handpiece in that the handpiece is provided with a locking recess with which a snap type element of the surgical instrument can be brought into detachable engagement. The locking recess may for instance be configured in the form of an annular groove; it is also possible to provide said groove only as a singular piece. The snap type element of the surgical instrument may e.g. be configured in the form of a snap type hook, a latch, or the like. Hence, upon insertion of the surgical instrument into the handpiece, a locking or coupling operation can be carried out that prevents an unintended detachment of the surgical instrument from the handpiece. To remove the surgical instrument from the handpiece, an actuating device must e.g. be operated.

The devices that are known from the prior art are often of a complicated construction and thus cost-intensive and intricate in their manufacture, and they are often difficult to handle when used in surgery.

Accordingly, what is needed is an improved surgical coupling device.

SUMMARY

In one embodiment, a surgical coupling device comprises first and second ends coupled by a body having a longitudinal axis, wherein an opening is formed along a portion of the body to provide access to a body recess within the body, and wherein the first end is sized to enter a coupling recess formed in a handpiece.

An actuator is positioned at least partially within the body recess and externally accessible via the opening, wherein the actuator includes a pivot element responsive to pressure applied to an outer surface thereof to pivot the actuator between a locked position and a released position. A double-sided rocker has an elevated support located so as to abut an inner surface of the body recess, wherein the elevated support is disposed between a coupling element of the double-sided rocker that is configured to engage a locking recess formed on an interior surface of the coupling recess when the actuator is in the locked position and an actuating element of the double-sided rocker that is configured to engage the actuator, wherein the double-sided rocker is aligned axially with respect to the actuator.

In another embodiment, a surgical instrument comprises first and second ends coupled by a body having a longitudinal axis, wherein an opening is formed along a portion of the body proximate the first end to provide access to a body recess within the body, and wherein the first end is sized to enter a coupling recess formed in a handpiece. An actuator is positioned at least partially within the body recess and externally accessible via the opening, wherein the actuator includes a pivot element responsive to pressure applied to an outer surface thereof to pivot the actuator between a locked position and a released position. A double-sided rocker is positioned at least partially within the recess and having a coupling element configured to engage a locking recess formed on an interior surface of the coupling recess when the actuator is in the locked position and an actuating element configured to engage the actuator.

In yet another embodiment, a surgical coupling device is provided for detachably connecting a handpiece to a surgical instrument. The handpiece has a recess into which a coupling portion of the surgical instrument can be detachably slid, wherein an interior wall of the recess includes a locking recess formed thereon. The surgical coupling device includes a snap type element configured to be brought into detachable engagement with the locking recess, wherein the snap type element is formed on a double-sided rocker that extends substantially in an axial direction and includes a first end on which the snap type element is formed and a second end on which an engagement element is formed for engagement with a pivot element.

DETAILED DESCRIPTION

Figure 1:
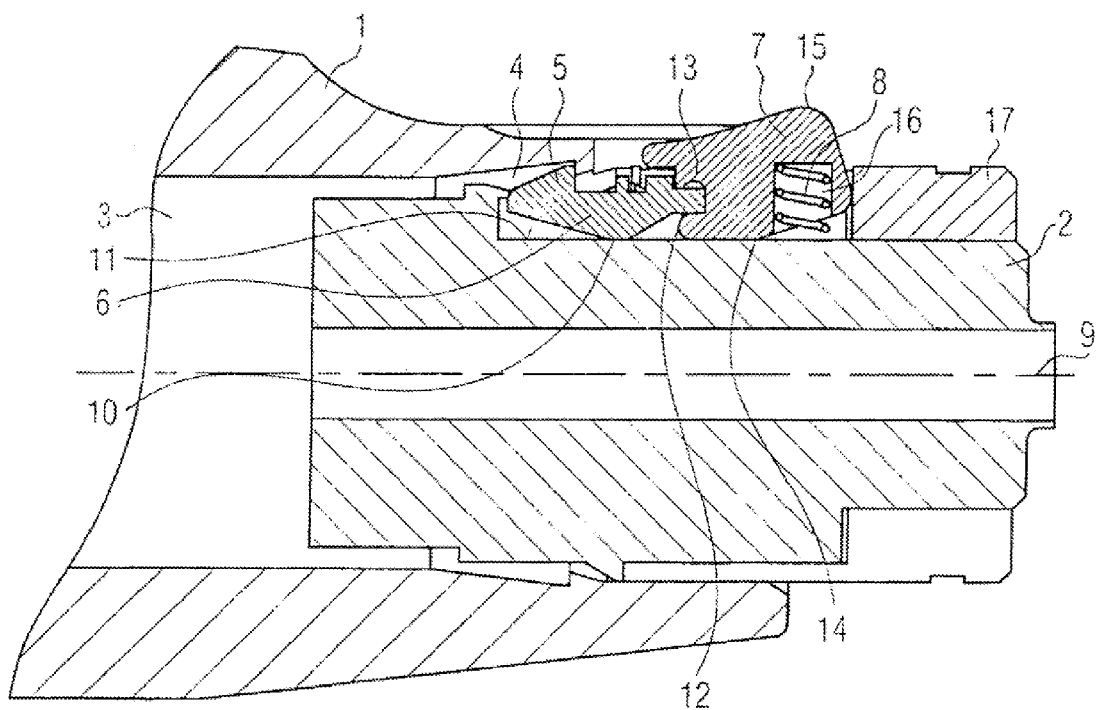
FIG. 1 illustrates an axial partial sectional view of one embodiment of the surgical coupling device.

It is one object of certain embodiments of the present invention to provide a surgical coupling device of the above-mentioned kind which while being of a simple construction and easily producible at low costs can be operated in a safe and easy manner.

According to the invention this object is achieved by the feature combination of the main claim; the subclaims show further advantageous developments of the invention.

Hence, according to the invention the snap type element is formed on a double-sided rocker which extends in axial direction and is thus pivotable about a rocker axis which is arranged to be substantially tangential or perpendicular to a central axis of the surgical coupling device. Thus the rocking movement of the rocker can bring the snap type element into engagement with the locking recess or release it from said recess.

At the other end, opposite to the end bearing the snap type element, the rocker is in engagement with a pivot element. Thus the pivot element defines the respective position of the rocker. The pivot element thereby brings the rocker into a locking position or a release position. In the locking position, the snap type element is located in the locking recess, thereby locking the surgical instrument with the handpiece. In the release position, the snap type element is not in the locking recess, so that the surgical instrument can be removed from the handpiece or slid into the handpiece.

Hence, either a locking or releasing operation is carried out through a selective movement of the rocker.

According to the invention it is intended that the rocker is actuable by means of a pivot element. To this end, as has been mentioned, the pivot element is in engagement with an end of the rocker. In a preferred variant of the invention, the pivot element is biased into an inoperative position in which the rocker is located in the locked position. The pivot element can be pivoted into a release position by being actuated. This will also cause the rocker to pivot because the rocker is in engagement with the pivot element. Hence, the rocker will also move into a release position.

In an advantageous variant of the invention, it is intended that the pivot element is biased by means of an elastic element into the inoperative position. The elastic element may be configured in the form of a spring which is positioned in a recess of the pivot element. Hence, a detachment of the snap type element from the locking recess just requires a corresponding pivoting of the pivot element. This can be carried out manually in an easy way. Hence, no complicated or sensible handling measures are needed, so that the surgical coupling device of the invention can also be handled in an easy and simple way in surgery.

In a particularly advantageous variant of the invention, it is intended that the rocker is provided at its side facing a central axis of the coupling device with a support portion which rests on a support surface of the surgical instrument. Next to the support portion, the rocker is preferably beveled at both sides. Thus the support portion forms a convex portion which is preferably line-shaped. This ensures a low-friction movement of the rocker between the locked position and the released position.

The engagement portion between the pivot element and the rocker is preferably designed such that the rocker is given a protruding form at its end facing the pivot element, resulting in a projecting edge or a projecting pin-like portion. This portion is arranged in a recess of the pivot element, resulting in an engagement in the manner of a joint. A pivot movement of the pivot element is thereby transmitted to the rocker. For this purpose the end of the rocker is moved in radial direction, based on the central axis of the coupling device.

For actuating or handling the pivot element, said element is preferably provided at its side facing the central axis also with a support portion resting on a support surface of the surgical instrument. The pivot element can thereby be pivoted or tilted. This leads to the described movement of the rocker for releasing or locking the snap type element.

It is particularly advantageous when the pivot element is provided with an actuating portion configured in the form of a knob or a grip. The latter can protrude to an appropriate degree beyond the circumferential surface of the surgical instrument, so that the pivot element can each time be actuated in a reliable manner.

Hence, the invention creates a surgical coupling device which enables the surgical instrument to reliably lock with the handpiece. The inserting operation may here be carried out either through a selective actuation of the rocker for releasing the snap type element or only by way of insertion. In the last-mentioned case, the snap type element, due to its being beveled, is automatically introduced into the locking recess. The detaching operation just requires an actuation of the actuating portion of the pivot element. Since the two elements (rocker and pivot element) form separate elements, a reliable function is ensured on the one hand, and an easy and inexpensive producibility on the other hand as only two components have to be arranged relative to one another.

The invention shall now be described with reference to an embodiment in combination with the drawing. FIG. 1 shows a cylindrical portion of a handpiece 1 which is provided with a substantially cylindrical central recess 3. A central axis of the handpiece 1 is illustrated by way of reference numeral 9.

The handpiece 1 may e.g. comprise a drive means, or the like, which may serve to couple and drive a surgical instrument 2.

The surgical instrument 2 is shown in FIG. 1 only schematically and in part. It comprises an end portion which is made substantially cylindrical and comprises a recess, which is e.g. axially slitted, including a support surface 11. The axially slit-like recess, which is not shown in detail, has arranged therein a rocker 6 which in being oriented radially inwards comprises an elevated support portion 10. The support portion 10 may establish line contact with the support surface 11. It is also possible to provide the support portion 10 with a radius as is shown in a simplified view in FIG. 1. Next to the support portion 10, the rocker 6 is each time beveled to perform a rocking movement in this way.

At its left end (based on FIG. 1), the rocker 6 has formed thereon a hook-like snap type element 5 which can be introduced into a locking recess 4 of the handpiece 1. In the illustrated embodiment, the locking recess 4 is shaped in the form of an annular groove. However, it is also possible to provide just a singular recess.

The end 12 of the rocker 6, which is the right one according to FIG. 1, is loosely inserted into a slit-like or fittingly shaped recess 13 of a pivot element 7. However, a hinge-like axial fixation might also be provided.

The pivot element 7 is provided at its radially inwardly oriented side with a support portion 14 which also shows point contact or line contact or surface contact with the support surface 11. At least one side of the interior portion of the pivot element 7 is beveled, as shown in FIG. 1, so as to be able to pivot the pivot element 7 accordingly. For manual operation the pivot element 7 comprises an actuating portion 15. Furthermore, the pivot element 7 is provided with a recess 16 accommodating an elastic element (spring) 8. The pivot element 7 is thereby biased into a position in which the rocker 6 is located in the locked position shown in FIG. 1. In pivoting or tilting the pivot element 7 by exerting pressure on the actuating portion 15, a pivotal or tilting movement is carried out, as a result of which the recess 13 will be radially moved outwards. This movement will also entrain the end 12 of the rocker 6 in a radially outwardly oriented direction, whereby the rocker 6 is pivoted around the support portion 10. This, in turn, has the effect that the snap type element 5 is detached from the locking recess 4.

To keep the rocker 6 and the pivot element 7 in place, a securing element 17, which may e.g. be configured as an annular or partly cylindrical member, is arranged on the surgical instrument 2.

The abstract of the disclosure is provided for the sole reason of complying with the rules requiring an abstract, which will allow a searcher to quickly ascertain the subject matter of the technical disclosure of any patent issued from this disclosure. It is submitted with the understanding that it will not be used to interpret or limit the scope or meaning of the claims.

Any advantages and benefits described may not apply to all embodiments of the invention. When the word "means" is recited in a claim element, Applicant intends for the claim element to fall under 35 USC 112, paragraph 6. Often a label of one or more words precedes the word "means". The word or words preceding the word "means" is a label intended to ease referencing of claims elements and is not intended to convey a structural limitation. Such means-plus-function claims are intended to cover not only the structures described herein for performing the function and their structural equivalents, but also equivalent structures. For example, although a nail and a screw have different structures, they are equivalent structures since they both perform the function of fastening. Claims that do not use the word means are not intended to fall under 35 USC 112, paragraph 6.

The foregoing description of the embodiments of the invention has been presented for the purposes of illustration and description. It is not intended to be exhaustive or to limit the invention to the precise form disclosed. Many combinations, modifications and variations are possible in light of the above teaching. For instance, in certain embodiments, each of the above described components and features may be individually or sequentially combined with other components or features and still be within the scope of the present invention. Undescribed embodiments which have interchanged components are still within the scope of the present invention. It is intended that the scope of the invention be limited not by this detailed description, but rather by the claims.

For instance, in some embodiments, there may be a surgical coupling device comprising: first and second ends coupled by a body having a longitudinal axis, wherein an opening is formed along a portion of the body to provide access to a body recess within the body, and wherein the first end is sized to enter a coupling recess formed in a handpiece; an actuator positioned at least partially within the body recess and externally accessible via the opening, wherein the actuator includes a pivot element responsive to pressure applied to an outer surface thereof to pivot the actuator between a locked position and a released position; and a double-sided rocker having an elevated support located so as to abut an inner surface of the body recess, wherein the elevated support is disposed between a coupling element of the double-sided rocker that is configured to engage a locking recess formed on an interior surface of the coupling recess when the actuator is in the locked position and an actuating element of the double-sided rocker that is configured to engage the actuator, wherein the double-sided rocker is aligned axially with respect to the actuator.

There may also be the surgical coupling device as above, wherein a bevelled surface extends from the elevated support to each of the coupling element and the actuating element.

There may also be the surgical coupling device as above, further comprising an elastic element abutting the actuator to bias the actuator into the locked position.

There may also be the surgical coupling device as above, wherein the elastic element is a spring captured in a retention recess formed in the actuator, wherein an end of the retention recess is open to allow the spring to abut the inner surface of the body recess.

There may also be the surgical coupling device as above, wherein the actuating element includes a protrusion and the actuator includes a recess designed to receive the protrusion.

There may also be the surgical coupling device as above, further comprising a securing element moveable between a first position preventing the actuator from moving from the locked position to the released position and a second position allowing the actuator to move from the locked position to the released position.

In yet other embodiments, there may be a surgical instrument comprising: first and second ends coupled by a body having a longitudinal axis, wherein an opening is formed along a portion of the body proximate the first end to provide access to a body recess within the body, and wherein the first end is sized to enter a coupling recess formed in a handpiece; an actuator positioned at least partially within the body recess and externally accessible via the opening, wherein the actuator includes a pivot element responsive to pressure applied to an outer surface thereof to pivot the actuator between a locked position and a released position; and a double-sided rocker positioned at least partially within the recess and having a coupling element configured to engage a locking recess formed on an interior surface of the coupling recess when the actuator is in the locked position and an actuating element configured to engage the actuator.

There may also be the surgical coupling device as above, wherein the double-sided rocker further comprises an elevated support positioned between the coupling element and the actuating element, wherein the elevated support is positioned to abut an inner surface of the body recess.

In yet other embodiments there may be a surgical coupling device for detachably connecting a handpiece to a surgical instrument, the handpiece having a recess into which a coupling portion of the surgical instrument can be detachably slid, wherein an interior wall of the recess includes a locking recess formed thereon, the surgical coupling device including a snap type element configured to be brought into detachable engagement with the locking recess, wherein the snap type element is formed on a double-sided rocker that extends substantially in an axial direction and includes a first end on which the snap type element is formed and a second end on which an engagement element is formed for engagement with a pivot element.

There may also be the surgical coupling device as above, wherein the pivot element is pivotable from an inoperative position into a release position.

There may also be the surgical coupling device as above, wherein the pivot element is biased into the inoperative position.

There may also be the surgical coupling device as above, wherein the pivot element is biased by means of an elastic element.

There may also be the surgical coupling device as above, wherein the elastic element is configured in the form of a spring positioned in a recess of the pivot element.

There may also be the surgical coupling device as above, wherein the rocker includes, on a side of the rocker facing a central axis of the coupling device, a support portion that rests on a support surface of the surgical instrument.

There may also be the surgical coupling device as above, wherein a surface of the rocker adjoining the support portion is bevelled at both sides of the support position.

There may also be the surgical coupling device as above, wherein the second end of the rocker includes a protruding form positioned in a recess of the pivot element.

There may also be the surgical coupling device as above, wherein the pivot element includes, on a side of the pivot element facing a central axis of the coupling device, a support portion that rests on a support surface of the surgical instrument.

There may also be the surgical coupling device as above, wherein the pivot element adjoining the support portion is bevelled on at least one side.

There may also be the surgical coupling device as above, wherein the pivot element includes an actuating portion.

There may also be the surgical coupling device as above, wherein the snap type element includes a frontal bevel.

What is claimed is:

1. A connection system for a surgical instrument comprising:
 a handpiece end including:
  a cylindrical recess defined within the handpiece end, the cylindrical recess having an interior surface,
  a locking recess defined within the interior surface,
 a portion of a surgical instrument sized to fit within the cylindrical recess of the handpiece end; the portion including:
  a support surface;
  a rocker comprising:
   a snap-type element,
   a rocker end,
   a beveled support portion positioned adjacent to the support surface,
  a pivot element comprising:
   a slit recess sized to enclose the rocker end,
   an actuating portion coupled to a biasing member wherein the biasing member bias the actuating portion away from the support surface,
   a beveled side
  a securing element for securing the pivot element to the surgical instrument.

2. The connection system of claim 1, wherein the actuating portion is pivotably moveable from a locked position wherein the biasing member bias the actuation portion away from the support surface to a position where the slit recess is moved away from the support surface.

3. The connection system of claim 1, wherein the rocker end is pivotably moveable outwards from the support surface such that the snap type element is moved out of the locking recess.

4. The connection system of claim 1, wherein the biasing member is a spring.

* * * * *